United States Patent
Bouduban et al.

(10) Patent No.: US 9,259,216 B2
(45) Date of Patent: Feb. 16, 2016

(54) ELONGATED FIXATION ELEMENT

(75) Inventors: Nicolas Bouduban, Langendorf (CH);
Dieter Schmidli, Oberdorf (CH);
Philippe Gedet, Langendorf (CH)

(73) Assignee: DePuy Synthes Products, Inc., Raynham, MA (US)

(*) Notice: Subject to any disclaimer, the term of this patent is extended or adjusted under 35 U.S.C. 154(b) by 717 days.

(21) Appl. No.: 13/339,003

(22) Filed: Dec. 28, 2011

(65) Prior Publication Data

US 2012/0191142 A1    Jul. 26, 2012

Related U.S. Application Data

(60) Provisional application No. 61/432,670, filed on Jan. 14, 2011.

(51) Int. Cl.
| | |
|---|---|
| *A61B 17/04* | (2006.01) |
| *A61B 17/84* | (2006.01) |
| *A61F 2/08* | (2006.01) |
| *A61B 17/064* | (2006.01) |
| *A61B 18/00* | (2006.01) |

(52) U.S. Cl.
CPC ......... *A61B 17/0401* (2013.01); *A61B 17/0642* (2013.01); *A61B 2018/00071* (2013.01); *A61B 2018/00089* (2013.01)

(58) Field of Classification Search
CPC ............ A61B 17/04; A61B 2018/00071; A61B 2018/00089; A61B 18/20; A61B 17/8685; A61B 17/8822; A61B 17/84; A61B 17/846; A61B 17/8605; A61B 17/8625

USPC .............. 606/300–321, 328, 329, 331, 139
See application file for complete search history.

(56) References Cited

U.S. PATENT DOCUMENTS

| | | | |
|---|---|---|---|
| 8,403,938 B2* | 3/2013 | Aeschlimann et al. ......... 606/93 |
| 8,777,618 B2 | 7/2014 | Baehre | |
| 2006/0095138 A1 | 5/2006 | Truckai et al. | |
| 2009/0018560 A1* | 1/2009 | Mayer et al. ................. 606/151 |
| 2009/0018590 A1* | 1/2009 | Dorawa et al. ............... 606/301 |
| 2009/0131947 A1* | 5/2009 | Aeschlimann et al. ......... 606/93 |
| 2009/0318912 A1* | 12/2009 | Mayer et al. .................... 606/14 |
| 2010/0023057 A1* | 1/2010 | Aeschlimann et al. ....... 606/246 |
| 2010/0082072 A1 | 4/2010 | Sybert et al. | |
| 2010/0241229 A1 | 9/2010 | Baehre | |

(Continued)

FOREIGN PATENT DOCUMENTS

| | | |
|---|---|---|
| CN | 101730551 A | 6/2010 |
| CN | 101801280 A | 8/2010 |
| WO | 2008/095327 | 8/2008 |

(Continued)

*Primary Examiner* — Kevin T Truong
*Assistant Examiner* — Si Ming Ku
(74) *Attorney, Agent, or Firm* — Baker & Hostetler LLP (57) ABSTRACT

A fixation device, having an elongated element extending along a central axis, having a total length L and including a proximal section formed of a material that is substantially non-absorbent for electromagnetic radiation within a preselected wavelength range and a distal section formed of a material that is substantially nonabsorbent for electromagnetic radiation within the preselected wavelength range in combination with a middle section axially arranged between the proximal and distal sections, the middle section formed of a material that is substantially absorbent for electromagnetic radiation in the preselected wavelength range.

19 Claims, 3 Drawing Sheets

(56) References Cited

U.S. PATENT DOCUMENTS

2012/0157977 A1* 6/2012 Hulliger ............... 606/13
2012/0226318 A1* 9/2012 Wenger et al. ........ 606/264

FOREIGN PATENT DOCUMENTS

WO 2008/112912 9/2008
WO 2009/036576 3/2009

* cited by examiner

ELONGATED FIXATION ELEMENT

PRIORITY CLAIM

The present application claims priority to U.S. Provisional Application Ser. No. 61/432,670 entitled "Elongated Fixation Element" filed on Jan. 14, 2011 to Nicolas Bouduban, Dieter Schmidli And Philippe Gédet, the entire disclosure of which is incorporated herein by reference.

FIELD OF THE INVENTION

The present invention generally relates to an elongated fixation element. More particularly, the present invention relates to an elongated fixation element comprising a middle section that absorbs electromagnetic radiation and two end sections that are non-absorbent. Exemplary embodiments of the invention relate to a process for producing the elongated fixation element and to a method for anchoring a suture to a bone using the elongated fixation element.

BACKGROUND

Implants or suture fasteners including heat bondable materials which are heated using lasers or other energy sources may be used to connect the implant or suture fastener with other implants and/or with bone. When heated, the heat bondable material softens (e.g., melts) into a surrounding bone material. In cases of poor bone quality, however, the softened portions of these devices may be unable to produce an adequate anchorage in such bone material.

Suture fasteners having a heat bondable material that may soften an area of the fastener surrounding the suture may have further disadvantages. For example, the suture may also melt, the suture may migrate in the softened fastener and the mechanical stability of the suture fastener may be adversely affected.

SUMMARY OF THE INVENTION

The present invention provides an elongated fixation element capable of being adequately anchored in poor bone stock. The task underlying the invention is to create an elongated fixation element having a distal portion which retains its mechanical strength as it is impacted into bone while another portion of the element may be softened and axially compressed to expand peripherally into the surrounding bone material, thereby producing a stable anchorage.

The present invention relates to an elongated fixation element extending along a central axis, having a total length L and comprising a distal section, a proximal section and a middle section axially arranged between the distal and proximal sections, wherein A) the proximal section is made of a material that is non-absorbent for electromagnetic radiation; B) the middle section comprises a material which is absorbent for electromagnetic radiation; and C) the distal section is made of a material that is non-absorbent for electromagnetic radiation.

One advantage of the invention lies in the fact that it can be anchored in a bone cavity independent of the quality of the bone material surrounding the cavity.

The elongated fixation element according to the invention, may be an implant such as, for example, a screw, pin, clip, prong, plate, nail, spiking wire, cage, pedicle screw (or nail), piercing, skin attachment, medicine carrier, gene material carrier, bioactive factor carrier (for instance growth factors, bone formation promoting substances, pain killers, etc., as carriers of other implants, as a dowel, clamp, pearl, dental implant, dental root implant, hose, tube, thread, thread in a hose or tube, tissue, web, skeleton, stocking, band, loose fibers, fibrous knot, fibrous flocks, granulate, chain, and anchor with or without a threading eyelet.

In an exemplary embodiment of the elongated fixation element, a material of the middle section comprises a polymer which:
(i) contains, at least partially, a colored substance; or
(ii) has a reflective coating; or
(iii) is self-colored; or
(iv) has a coating capable of receiving colored substances in contact with body fluids containing colored substances.

In another exemplary embodiment of the elongated fixation element, the material of the middle section is a thermoplastic material.

In another exemplary embodiment of the elongated fixation element, the thermoplastic material is polymethylmethacrylate.

In a further exemplary embodiment of the elongated fixation element, the thermoplastic material is chosen from the following groups: poly-alpha-hydroxyester, polyorthoester, polyanhydride, polyphosphazenes, poly(propylenefumarate), polyesteramide, polyethylenefumarate, polylactide, polyglycolide, poly(lactic-co-glycolic acid), polycaprolacton, trimethylenecarbonate, polydioxanone, polyhydrobutyrate, as well as their copolymers and admixtures.

In a further exemplary embodiment of the elongated fixation element, the middle section is made fully of a polymeric or copolymeric material.

In yet a further exemplary embodiment of the elongated fixation element, the element is made entirely of a polymeric or copolymeric material.

In yet a further exemplary embodiment of the elongated fixation element, the electromagnetic radiation has a wavelength in the range of approximately 400 to approximately 1300 nm.

In still a further exemplary embodiment of the elongated fixation element, the middle section is meltable at a temperature in the range of approximately 50° C. to approximately 250 C.°.

In another exemplary embodiment of the elongated fixation element, the proximal section and the distal section have a diameter D and are connected by a bridge having a reduced diameter d<D about which the meltable material of the middle section is arranged.

In another exemplary embodiment of the elongated fixation element, the ratio D/d is larger than approximately 2, and preferably larger than approximately 3.

In another exemplary embodiment of the elongated fixation element, the ratio D/d is smaller than approximately 7.5, preferably smaller than approximately 6. Typically, D is in the range of approximately 1 to approximately 10 mm and d is in the range of approximately 0.5 to approximately 3 mm.

In yet another exemplary embodiment of the elongated fixation element, the non-absorbent material has a volume V in the range of approximately 1 to approximately 500 mm$^3$ and the absorbent material has a volume v in the range of approximately 1 to approximately 400 mm$^3$.

In yet another exemplary embodiment of the elongated fixation element, the distal section has an axial length of approximately 0.06 L to approximately 0.15 L.

In yet another exemplary embodiment of the elongated fixation element, the middle section has an axial length of approximately 0.50 L to approximately 0.70 L.

In a further exemplary embodiment of the elongated fixation element, the proximal section has an axial length of approximately 0.25 L to approximately 0.35 L.

In a further exemplary embodiment of the elongated fixation element, the distal section comprises a suture.

In a further exemplary embodiment of the elongated fixation element, the distal section includes a transverse through hole. In one embodiment, the hole has a hole axis in a plane orthogonal to the central axis.

In yet a further exemplary embodiment of the elongated fixation element, the suture passes through the transverse through hole.

In another exemplary embodiment of the elongated fixation element, a mirror is arranged between the middle section and the distal section to reflect electromagnetic radiation that passes through the middle section back to the middle section.

In another exemplary embodiment the elongated fixation element is designed as a bone fixation element, preferably in the form of a bone screw, bone rod, bone dowel, pin, plate, dowel, hose, tube, thread, thread in a hose or tube, a bone anchor, a dental implant or a dental root implant.

According to a further aspect of the invention, there is provided a process for producing an elongated fixation element according to invention, comprising the steps of a) producing the distal section, middle section and proximal section each separately by injection molding and b) fixing the distal section axially to one end of the middle section and the other end of the middle section to the proximal section to form the elongated fixation element by gluing.

According to yet a further aspect of the invention, there is provided a further process for producing an elongated fixation element according to the invention, comprising the steps of a) producing the proximal section and the middle section as one piece by injection molding; b) modifying the middle section to comprise a material which is essentially absorbent for a predetermined frequency range of electromagnetic radiation; c) producing the distal section by injection molding; and d) fixing the distal section axially to the free end of the middle section by gluing.

In accordance with another aspect of the present invention, a process is provided for producing an elongated fixation element according to the invention, comprising the steps: a) preparing a convertible mold for injection molding of a first part comprising the distal section and the proximal section connected by the bridge; b) producing the first part comprising the distal section and the proximal section connected by the bridge by injection molding; c) converting the convertible mold for injection molding of the middle section onto the first part produced under step b); and d) producing the middle section onto the first part by injection molding.

According to yet another exemplary aspect of the invention, there is provided a method for anchoring a suture to a bone comprising the following steps: a) drilling a hole with a diameter DH into a bone; b) inserting a portion of a suture into the hole in the bone; c) heating an elongated fixation element according to the invention with a diameter slightly larger than or equal to DH by means of radiation energy to thereby soften the middle section of the elongated fixation element; d) pressing the softened elongated fixation element into the hole in the bone; and e) switching off or removing the heat source and allowing cooling off of the elongated fixation element.

According to yet another aspect of the invention, there is provided a method for anchoring a suture to a bone comprising the following steps: a) drilling a hole with a diameter DH into a bone; b) inserting a strand of a suture into a transverse through hole of an elongated fixation element according to the invention with a diameter slightly larger than or equal to DH; c) heating the elongated fixation element via radiation energy to soften the middle section of the elongated fixation element; d) pressing the softened elongated fixation element into the hole in the bone; and e) switching off or removing the heat source, allowing the elongated fixation element to cool.

The following definitions apply to the following terms frequently employed in the entire description:

Softening: Softening of the implant material according to the invention refers to the softening of the implant resulting from the heat generated by the absorption of radiation. In particular, the softening permits a previously unusably plastically deformable implant (e.g., deformable by hand) to be deformed and employed according to the invention, as described below.

Optical waveguide: The term optical waveguide refers to flexible or rigid optical light-transmitting structures such as, for example, glass fiber cables or reflecting hoses (e.g. also nano-tubes) used to transmit electromagnetic radiation from the source to the fastener. The fastener itself, however, may also serve as an optical fiber and light diffuser. For example, light may enter the fastener and be transmitted through the non-absorbent part of the fastener until it arrives at the point where the softening of the polymer is to take place.

Light source: All sources of electromagnetic radiation may be considered suitable light sources. Suitable light sources may be, for example, incandescent light bulbs, vapor emission lamps, diodes, semiconductors, sparks, flames, sunlight etc.

Laser types: Lasers are preferred sources of energy, as they typically emit only a few narrowly defined frequencies of electromagnetic radiation. The absorption spectra of the chromophore of the non-absorbing portion of the implant as well as the body's surroundings may thus be tuned to each other. In one application, the laser radiates in a monochromatic frequency that is barely absorbed by the implant, strongly absorbed by the chromophore, and again minimally absorbed by the surroundings. Thus, it is possible to supply different areas of the implant with different chromophores so that they may be individually heated by applying the corresponding frequency of electromagnetic radiation frequency as required on a case-by-case basis.

One or more of the radiation frequencies that are especially well absorbed by the chromophore pigment in the polymer or by the light-absorbing polymer are particularly preferred.

The use of any currently known laser type (e.g., swinging mode lasers, pulsating lasers or continuous wave lasers) is contemplated. For example, the lasers may be diode lasers of the infrared or visible spectrum. Under certain conditions, it may be desirable to employ polarized radiation by, for example, including polarization filters in the implant or on the radiating source, or by generating electromagnetic radiation in polarized form. The polarization may be utilized as a way of selecting the targeted warming-up of the implant, especially when employing chromophores that are excitable by polarized light.

The wavelength of the electromagnetic radiation may lie in a range between 260 and 3,000 nm, and preferably in the range of 400 to 1,300 nm. The shape of the light radiation may have any of a variety of shapes such as, for example, a cross section of an oval, rectangular, star-shaped, triangular, bundle-shaped form, etc.

A non-exhaustive list of employable lasers is shown below:

| | Wavelength(s) |
|---|---|
| Gas laser | |
| Helium-neon laser | 632.8 (543.5 nm, 593.9 nm, 611.8 nm, 1.1523 µm, 1.52 µm, 3.3913 µm |
| Argon laser | 454.6 nm, 488.0 nm, 514.5 nm, 457.9 nm, 465.8 nm, 476.5 nm, 472.7 nm, 528.7 nm) |
| Krypton laser | 416 nm, 530.9 nm, 568.2 nm, 647.1 nm, 676.4 nm, 752.5 nm, 799.3 nm |
| Xenon ion laser | Various wavelengths from UV to infrared |
| Nitrogen laser | 337.1 nm |
| Carbon dioxide laser | 10.6 µm (9.4 µm) |
| Carbon monoxide laser | 2.6 to 4 µm, 4.8 to 8.3 µm |
| Exciter laser | |
| Chemical lasers | |
| Hydrogen fluoride laser | 2.7 to 2.9 µm, |
| Deuterium fluoride laser | ≈3800 nm (3.6 to 4.2 µm) |
| COIL (Chemical oxygen-iodine laser) | 1.315 µm |
| Color laser | |
| Color laser | 390-435 nm (stilbene), 460-515 nm (coumarin 102), 570-640 nm (rhodamine 6G, and others |
| Metal-vapor laser | |
| Helium-cadmium (HeCd) metal-vapor laser | 441.563 nm, 325 nm |
| Helium-mercury (HeHg) metal-vapor laser | 567 nm, 615 nm |
| Helium-selenium (HeSe) metal-vapor laser | Up to 24 wavelengths between red and UV |
| Copper-vapor laser | 510.6 nm, 578.2 nm |
| Gold-vapor laser | 627 nm |
| Solid material laser | |
| Ruby laser | 694.3 nm |
| Nd: YAG laser | 1.064 µm, (1.32 µm) |
| Er: YAG laser | 2.94 µm |
| Neodymium YLF (Nd: YLF) sold material laser | 1.047 and 1.053 µm |
| Neodymium-doped Yttrium orthovanadate (Nd: YVO$_4$) laser | 1.064 µm |
| Neodymium-doped Yttrium calcium oxoborate laser, Nd: YCa$_4$O(BO$_3$)$_3$ or simply Nd: YCOB | ≈1.060 µm (≈530 nm at the second harmonic |
| Neodymium glass (Ti: sapphire) laser | 650-1100 nm |
| Titanium sapphire (Ti: sapphire) laser | ≈1.062 µm (silicate glasses), ≈1.054 µm (phosphate glasses) |
| Thulium YAG (Tm: YAG) laser | 2.0 µm |
| Ytterbium YAG (Yb: YAG) laser | 1.03 µm |
| Ytterbium doped glass laser (rod, plate/chip, and fiber) | 1 µm |
| Holmium YAG (Ho: YAG) laser | 2.1 µm |
| Cerium-doped lithium strontium (or calcium) aluminum fluoride (Ca: LiSAF, Ce: LiCAF) | ≈280 to 316 nm |
| Promethium 147 doped phosphate glass ($^{147}$Pm$^{+3}$. Glass) solid-state laser | 933 nm, 1098 nm |
| Chromium doped and erbium-ytterbium co doped glass lasers | 1.53-1.56 µm |
| Trivalent uranium doped calcium fluoride (U: CaF$_2$) solid state laser | 2.5 µm |
| Divalent samarium doped calcium fluoride (Sm: CaF$_2$) laser | 708.5 nm |
| F-center laser | 2.3-3.3 µm |
| Semiconductor laser | |
| Semiconductor laser diode | 0.4-20 µm, depending on the material |
| GaN | 0.4 µm |
| AlGaAs | 0.63-0.9 µm |
| InGaAsP | 1.0-2.1 µm |
| Lead salt | 3-20 µm |
| Vertical cavity surface emitting laser (VCSEL) | 850-1500 nm, depending on the material |
| Quantum cascade laser | Infrared |
| DPSS-laser | UV-infrared |
| Hybrid silicon laser | Infrared |

Absorption of electromagnetic radiation: The term absorption of electromagnetic radiation indicates that the implant typically (but not necessarily) absorbs at least twice as much irradiated energy as absorbed in the areas indicated as nonabsorbent. More specifically, however, 5-1000 times more energy may be absorbed in the energy-absorbing areas than in the areas indicated as nonabsorbent. This difference in radiation absorption is indicated only in regard to the frequency of radiation to be applied to the absorbent sections. Absorption characteristics of the nonabsorbent portions with regard to other frequencies of radiation need not differ at all from the absorption characteristics of the absorbent portions.

For example, in non-absorbing areas the implant may absorb 0-10% of the irradiated energy while in areas including a chromophore (absorbent areas) 50-100% of the energy is absorbed while the residual energy leaves the implant and to escape into the surroundings.

Chromophore: The term chromophore refers to colors or pigments added to a polymer to absorb a corresponding frequency of electromagnetic radiation and convert this energy to heat.

Chromophores (e.g., colors and pigments) may includes, for example, chlorophyll, carbon black, graphite, fluorescein, methylene blue, indocyanine green, eosine; eosine Y (514 nm), ethyleosine (532 nm), acridine, acridine orange, copper phtalocyanine, chrome-cobalt-aluminum oxide, ferrous ammonium citrate, pyrogallol, logwood extract, chlorophyll-copper complex, D&C blue No. 9, D&C green No. 5, [phtalocyaninate(2-)] copper, D&C blue no. 2, D&C blue no. 6, D&C green no. 6, D&C violet no. 2, D&C yellow No. 10. A special case are the fluorescent chromophores which, under certain circumstances, do not absorb but radiate light that is absorbed by the surroundings, the polymer or any additionally introduced chromophore.

One exemplary application employs substances that are added to the implant or coated thereon, which do not have chromophore properties. These substances change upon contact with the body, for example, as a result of a reaction to the pH of the tissue, to body salts, body moisture or body temperature, discoloring the substance so that it becomes absorbent to the desired frequency of electromagnetic radiation. Thus, the only areas heated are areas that come into contact with the body since the implant becomes discolored only at that point.

Light-absorbing, non-colored polymer: Light-absorbing polymers refer to polymers having a property of their own to absorb light of a certain wavelength, without the addition of a chromophore. In one application, the polymer is heated until the polymer spontaneously discolors, becoming capable of absorbing more light. In an extreme case, the polymer is partially carbonized or caramelized and thus becomes light-absorbent.

The absorption coefficient of the polymers is, like that of the chromophore, variable and must be set based on the indications. Indocyanine, for instance, has an absorption coefficient of 20,000 $mg^{-1}\ cm^{-1}$. The resulting absorption coefficient of the polymer also depends on the concentration of the polymer in the implant. A typical range is between 1,000 and 1,000,000 $mol^{-1}\ cm^{-1}$.

Porous surface: The term porous surface refers to a surface which is suitable, after contacting the body's surface or body fluids (e.g., blood), for heating by irradiation with an electromagnetic radiation. This occurs when, upon contact with the body, the implant is contaminated and becomes light-absorbing at the contaminated point. Before contacting the body, this particular embodiment of the implant has little or no capability to be heated by the selected frequency of electromagnetic radiation. Surfaces particularly suited for this embodiment of the implant may include, for example, rough, porous, uneven, spongy surfaces, which are eventually coated with hydrophilic, highly absorbent materials such as for instance calcium phosphates, other ceramics, gypsum etc. Alternatively, it is also possible to include structural elements through which body fluids are drawn or flow into the interior of the implant (e.g., blood, through capillary forces) and absorbing light inside the same. As a result of the implant's deformation when pressed into the body or when creating the desired connection, the chromophore structures from the body are blended with the implant surface, thus reinforcing the local heating effect. Surprisingly, at a suitable wavelength, areas of the body in the immediate vicinity of the implant were also heated since the wavelength was chosen so that the body fluids contacting the implant, or the contacting body surface interacting with the implant's surface, absorbed the electromagnetic radiation. It is, however, possible via a suitable impulse duration and wavelength (or a combination of wavelengths) to achieve heating only in the immediate vicinity (<1 mm), without significantly damaging the tissue. This heating, which should preferably not exceed 100° C. and even more preferably 56° C., facilitates flow of the softened thermoplastic material into the interspaces of the body surface. This effect may also be achieved in the other embodiments mentioned above and below, when the electromagnetic radiation frequencies as well as the pulsating type, frequency and duration and the quantity of energy are appropriately chosen. According to the invention, the porous surface which may be, for example, a calcium phosphate coating, is combined with a chromophore, either as an additional coating or as an admixture.

Frequency modulation: To achieve a local heating of the implant, substances or optical elements may be introduced into the implant which, while does not significantly absorb electromagnetic radiation, possesses the property of shifting the frequency of light by, for example, frequency doubling crystals or multiplying crystals. In this case, the long-wave light passes through the implant to the area with the frequency changing (normally doubling) characteristic without significantly heating it, then heats it and leaves the same, to a certain percentage, with a somewhat shorter frequency, while being absorbed to a significantly greater degree from the remainder of the implant. This effect can also be repeated several times. Some substances that may be used for frequency modulation are non-linear optical substances such as, for example, lithium niobate ($LiNbO_2$), potassium dihydrogen phosphate (KDP), lithium triborate or DAST (diethylammino-sulfurtrifluoride). Similarly, even phase transitions or boundary layers having the same effect can be integrated inside or on the implant.

Energy: The energy required to adequately heat the implant depends on a size of the implant, application and structure and/or quality of the bone in which the implant will be inserted. The typical average power of a light source is as follows: for small pins or fixation elements (of a diameter of 0.1-5 mm): about 0.1-50 Watt and preferably 0.5-10 Watt, and for the fixation of large prostheses or filling large bone defects 1-2,000 Watt.

The peak power during individually applied pulses may attain 5 kW and more. The target is to soften a polymer having a softening volume V with an alternating current having a power density $P=0.005-5\ Watt/mm^2$, within about 0.1-10 seconds. The energy E applied therefore equals about $E=0.0005-50\ Watt*seconds/mm^3$.

Reflectingly coated polymer: A reflecting coating refers to a polymer coating which inhibits the emission of electromagnetic radiation so that the light is retained in the polymer and can heat the polymer even at a low level of absorption (optionally even without a chromophore). However, the reflecting coating may also be used in combination with a chromophore and reinforce the action of the chromophore. In a further exemplary embodiment, the implant may be treated with a reflecting coating to prevent a premature emission of light from the implant to, for example, conduct the light toward the implant's tip. The reflection acts to reinforce the photo-conductance inside the implant.

Materials for a reflecting coating (which can also be worked into the interior of the polymer) may include all light-reflecting substances such as, for example, metals and especially metals compatible with the body, such as gold, titanium, platinum silver, steel and its alloys.

A medical implant according to the present invention may be used to provide rotator cuff repair, labral repair, fixation of patches, subchondral fractures treatment, ACL/PCL reconstruction, fracture fixation, fracture reduction and reposition.

BRIEF DESCRIPTION OF THE DRAWINGS

The invention and improvements of the invention will be described in greater detail below, with the aid of the drawings of various examples of embodiments, in which.

DETAILED DESCRIPTION

The present invention may be further understood with reference to the following description and the appended drawings, wherein like elements are referred to with the same reference numerals. The present invention relates to a fixation device and, in particular, to a fixation device including an electromagnetic radiation absorbing portion which softens to fix the fixation device within or on a bone. Exemplary embodiments of the present invention describe an elongated fixation device including non-absorbent proximal and distal sections and an absorbent middle section arranged therebetween, which softens and/or melts into a surrounding bone when heat-activated. The terms "proximal" and "distal" as used herein are intended to refer to a direction toward (proximal) an away from (distal) a surgeon or other user of the device.

Figure 1:
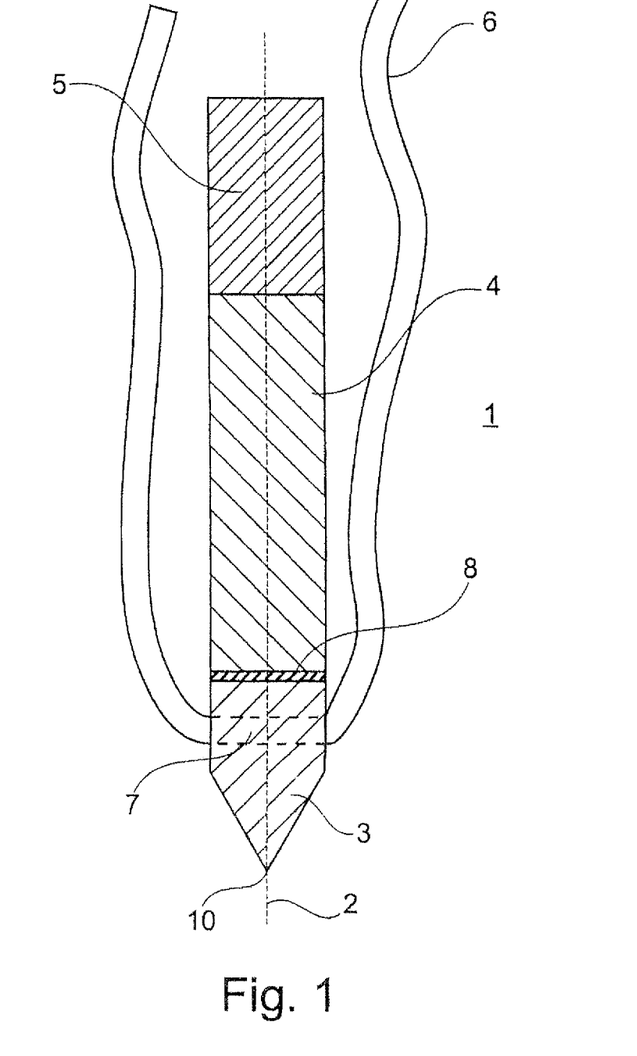
FIG. 1 illustrates a longitudinal section through an elongated fixation element according to a first exemplary embodiment of the invention before implantation.
Figure 2:
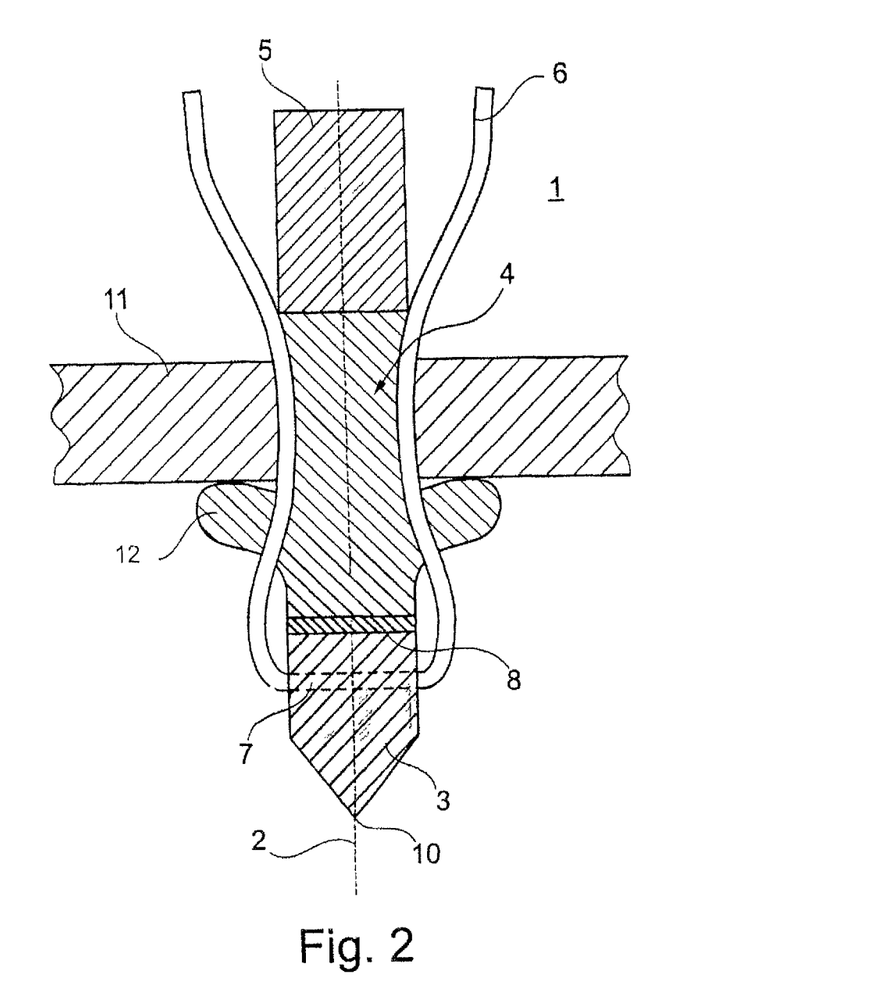
FIG. 2 illustrates a longitudinal section through the elongated fixation element according to FIG. 1 after implantation through the near cortex of a bone, softening, compressing and cooling.

As shown in FIGS. 1-2, an elongated fixation element 1 according to an exemplary embodiment of the present invention extends along a central axis 2 and comprises a distal section 3, a proximal section 5 and a middle section 4 axially arranged between the distal and proximal sections 3, 5. The elongated fixation element 1 is designed as a bone fixation element, in the form of a pin with a pointed tip 10 at a distal end of the distal section 3. The proximal section 5 may be configured to connect to a light source such as, for example, a laser device for transmitting electromagnetic radiation to the elongated fixation element 1. The element 1 may be formed of a polymeric or copolymeric material wherein the material of the middle section 4 is a thermoplastic material. Thus, the proximal section 5 and distal section 3 are non-absorbent for electromagnetic radiation while the middle section 4 is absorbent for electromagnetic radiation and is meltable at a temperature preferably in the range of about 50° C. to about 250° C. The electromagnetic radiation can have a wavelength in the range of 400 to 1300 nm. Thus, the elongated fixation element 1 is transformable from a first insertion configuration, as shown in FIG. 1, to a second activated configuration, as shown in FIG. 2, in which the middle section 4 absorbs the electromagnetic radiation to soften and/or melt into a surrounding bone material.

The elongated fixation element extends along a total length L. The distal section 3 may have an axial length of about 0.15 L. The middle section 4 may have an axial length of about 0.60 L and the proximal section 5 may have an axial length of about 0.25 L. In the first insertion configuration, the proximal, middle and distal sections 5, 4, 3 may have substantially similar diameters such that the elongated fixation element 1 may have a substantially consistent diameter along a length thereof. The distal section 3 includes a transverse through hole 7, which may have a central hole axis arranged in a plane substantially orthogonal to the central axis 2 of the fixation element 1. A suture 6 may be passed through the transverse through hole 7. Alternatively, the suture 6 may not be passed through the transverse through hole 7 and used separately from the elongated fixation element 1. In a further embodiment, the fixation element 1 may also comprise a mirror 8 arranged between the middle section 4 and the distal section 3 to prevent any electromagnetic radiation passing through the middle section 4 from also passing through the distal section 3. The mirror 8 reflects the electromagnetic radiation that passes through the middle section 4 back to the middle section 4. As shown in FIG. 2, upon activation of the elongated fixation element 1 via the electromagnetic radiation, the middle section 4 softens and expands outward into a surrounding bone material such that the elongated fixation element 1 and/or the suture 7 is fixed therein. Exemplary surgical techniques using the elongated fixation device 1 are described in the examples below.

Each of the proximal, middle and distal sections 5, 4, 3 may be formed separately using an injection molding process and attached to one another to form the elongated fixation element 1. The absorbent material may be added to the middle section 4 during the injection molding process via, for example, a chromophore or a light absorbing polymer. In another embodiment, the absorbent material may be added as a coating applied to the middle section 4. Alternatively, the elongated fixation element 1 may be integrally formed using a similar injection molding process. The middle section 4 may then be modified to include the absorbent material capable of absorbing electromagnetic radiation to soften.

Figure 3:
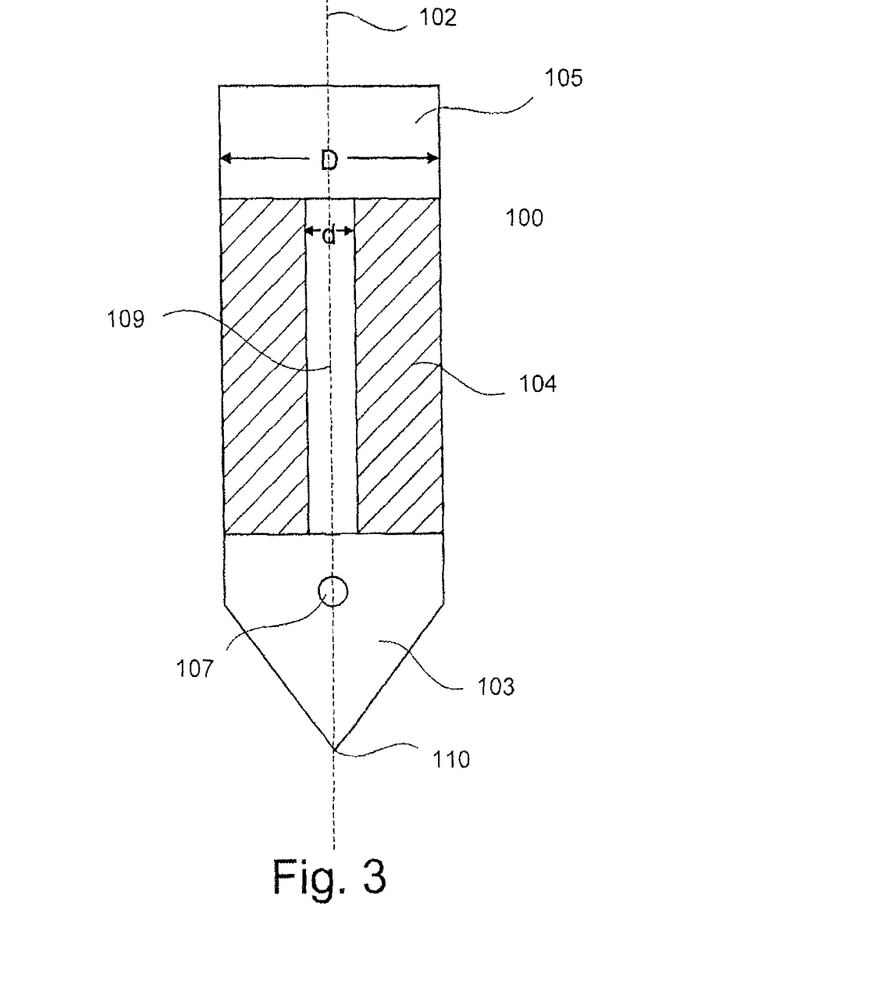
FIG. 3 illustrates a longitudinal section through an elongated fixation element according to a second exemplary embodiment of the invention before implantation.

As shown in FIG. 3, an elongated fixation element 100 may be substantially similar to the elongated fixation element 1 described above in regard to FIGS. 1 and 2. Similarly to the elongated fixation element 1, the elongated fixation element 100 extends along a central axis 102 and comprises a proximal section 105, a distal section 103 and a middle section 104 arranged between the proximal and distal sections 105, 103. The distal section 103 may include a pointed distal tip 110 and a transverse through hole 107 sized and shaped to receive a suture therethrough. The elongated fixation element 100 differs from the elongated fixation element 1 of FIGS. 1 and 2 only in that the proximal section 105 and the distal section 103 are connected by a bridge 109 around which the meltable material of the middle section 104 is arranged. The proximal and distal sections 105, 103 have a diameter D while the bridge 109 has a reduced diameter d<D. The reduced diameter bridge 109 is surrounded by the absorbent material of the middle section 104. The reduced diameter bridge 109 will also melt as heat is transmitted from the surrounding middle section 104. The diameter d of the bridge 109 may be in a range of about 0.5 mm to about 2.0 mm and the diameter D of the larger distal and proximal sections 103, 105 may be in a range of about 3 mm to about 10 mm. A suitable ratio D:d may therefore be in the range of about 4.0 to about 7.5, preferably of about 5 to about 6.

The elongated fixation element 100 may be molded using a similar injection molding process, as described above in regard to the elongated fixation element 1. The proximal and distal sections 105, 103 along with the bridge 109 may be formed using a convertible mold. After molding the proximal and distal sections 105, 103 and the bridge 109, the mold may be converted such that the middle section 104 may be molded over the bridge 109. The absorbent material of the middle section 104 may be added during the molding process. Alternatively, the middle section 104 may be modified after molding to include the absorbent material. The examples below specifically describe surgical techniques using the elongated fixation device 1. However, it will be understood by those of skill in the art that the elongated fixation device 100 may be used in a similar manner.

EXAMPLE 1

Bone Anchor

The elongated fixation element 1 may be utilized to fix the suture 6 to a bone to fasten a tendon or other bone portion with the suture 6. In one example, a hole having a diameter of 3 mm and a depth up to 15 mm may be drilled into the bone. The suture 6 with a high melting point may be inserted into the hole drilled in the bone. An elongated fixation element 1, which has a slightly greater diameter than the drilled hole may then be positioned over the hole drilled in the bone. The elongated fixation element 1 may then be heated up by applying radiant energy to the proximal section 5 of the elongated fixation element 1 using a light diode. Upon softening of the middle section 4 by the radiation energy, the elongated fixation element 1 may be pressed through the drilled hole and into the bone. Once the light source is turned off, the middle section 4 solidifies and the elongated fixation element 1 is fixed to the bone together with the suture 6. Although the example specifically describes a hole having a diameter of 3 mm and a depth up to 15 mm, it will be understood by those of skill in the art that a user may use a similar technique for fixing the suture 6 to the bone by creating a hole of any size and shape so long as a size of the elongated fixation element 1 is selected to correspond thereto.

EXAMPLE 2

Bone Anchor

In another example for fastening a tendon or other bone portion using a suture 6, the suture 6 may be passed through a transverse through hole 7 in the elongated fixation element 1. The elongated fixation element 1 may then be inserted into the bone and fastened thereto by activating the middle section 4 using an optical waveguide, e.g. a glass fiber connected to a light source or a laser source. The optical waveguide may be connected to a proximal face of the proximal section 5 or inserted in a bore in the proximal section 5 of the elongated fixation element 1. The torn-off tendon may then be fastened to the bone using the suture 6. With the suture 6 fastened to the tendon, the elongate fixation element 1 is pressed into the bone. Pressing the elongate fixation element 1 into the bone causes the suture 6, in this case, to be fastened under a tension force. That is, pressing the implant into the bore of the bone tensions the suture and the tendon attached with the suture. Due to the application of light via the proximal section 5 of the elongated fixation element 1, the middle section 4 of the elongated fixation element 1 is partially molten and is simultaneously glued under slight pressure to the suture 6. Thus, the elongated fixation element 1 and the suture 6 are both fixed in the bone. After cooling for approximately 30 seconds the elongate fixation element 1 is fixed in position. At this stage, the tension force on the suture 6 can optionally be adjusted.

EXAMPLE 3

In another example, the elongated fixation element 1 in the form of a suture fastener, as shown in FIGS. 1-2, is impacted through the cortex 11 of a bone via the distal tip 10. Laser light is then directed through the transparent proximal section 5 to the middle section 4, which is softened by absorption of the laser light. Upon softening of the middle section 4, the suture 6 passing through the transverse hole 7 of the distal section 3 is pulled proximally so that the distal section 3 which has retained its mechanical integrity compresses the softened material of the middle section 4 which expands in diameter and forms a circumferential ring-like body 12 which abuts against an inner surface of the cortex 11 as shown in FIG. 2. After cooling off, the softened material of the middle section 4 the suture fastener is firmly fixed in the bone and is prevented from being pulled out of the bone by the circumferential ring like body 12 which abuts against the inner surface of the cortex 11.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. A fixation device configured for insertion into bone, the fixation device comprising:
    an elongated element extending along a central axis, having a total length L and including:
        a proximal section that is solid along the central axis and is substantially non-absorbent of electromagnetic radiation within a preselected wavelength range;
        a distal section formed of a material that is substantially non-absorbent of electromagnetic radiation within the preselected wavelength range, the distal section including a pointed distal tip at a distal-most point along the central axis, the pointed distal tip configured to be impacted through a cortex of the bone; and
        a middle section that is solid along the central axis and is axially arranged between the proximal and distal sections so as to space and separate the proximal section from the distal section along the central axis, thereby causing the proximal section, the distal section, and the middle section to be axially aligned with one another along the central axis, the entire middle section formed of a material that is substantially absorbent of electromagnetic radiation within the preselected wavelength range,
    wherein the elongated element defines a first configuration before an application of electromagnetic radiation within the preselected wavelength range and a second configuration after the application of electromagnetic radiation within the preselected wavelength range,
    i) such that in the first configuration, the middle section of the elongated element is positionally fixed relative to the proximal and distal sections, and ii) such that in the second configuration, the middle section softens and melts in response to the application of the electromagnetic radiation within the preselected wavelength range.

2. The device according to claim 1, wherein the material of the middle section comprises one of (i) a polymer containing at least partially a substance colored to absorb electromagnetic radiation within the predetermined wavelength range, (ii) a polymer including a reflecting coating, (iii) a polymer self-colored to absorb electromagnetic radiation within the predetermined wavelength range; and (iv) a polymer having a coating receiving colored substances from body fluids in contact therewith, the preselected wavelength range being selected to be absorbed by the polymer after it has received the colored substances from the bodily fluids.

3. The device according to claim 2, wherein the material of the middle section is a thermoplastic material.

4. The device according to claim 3, wherein the thermoplastic material is at least one of polymethylmethacrylate, poly-alpha-hydroxyester, polyorthoester, polyanhydride, polyphosphazenes, poly(propylenefumarate), polyesteramide, polyethylenefumarate, polylactide, polyglycolide, poly(lactic-co-glycolic acid), polycaprolacton, trimethylenecarbonate, polydioxanone and polyhydrobutyrate.

5. The device according to claim 1, wherein the middle section is entirely formed of one of a polymeric and a copolymeric material.

6. The device according to claim 5, wherein the entire device is formed of one of a polymeric and a copolymeric material.

7. The device according to claim 1, wherein the preselected wavelength range is from 400 to 1300 nm.

8. The device according to claim 1, wherein the middle section melts at a temperature in the range of 50° C. to 250° C.

9. The device according to claim 1, wherein the proximal section and the distal section have a diameter D and are connected by a bridge of reduced diameter d<D around which the middle section is arranged.

10. The device according to claim 9, wherein the ratio D/d is one of larger than 2 and larger than 3.

11. The device according to claim 9, wherein the ratio D/d is one of smaller than 7.5 and smaller than 6.

12. The device according to claim 1, wherein the non-absorbent material has a volume V in the range of 1 to 500 $mm^3$ and the absorbent material has a volume v in the range of 1 to 400 $mm^3$.

13. The device according to claim 1, wherein the distal section has an axial length of 0.06 L to 0.15 L, the middle section has an axial length of 0.50 L to 0.70 L and the proximal section has an axial length of 0.25 L to 0.35 L.

14. The device according to claim 1, the device further comprising a suture.

15. The device according to claim 14, wherein the distal section comprises a transverse through hole sized and shaped to receiving the suture therethrough.

16. The device according to claim 15, wherein the transverse through hole has a hole axis arranged in a plane substantially orthogonal to the central axis.

17. The device according to claim 1, the device further comprising a mirror arranged between the middle section and the distal section to reflect electromagnetic radiation that passes distally through the middle section proximally back into the middle section.

18. The device according to claim 1, wherein the elongated element is one of a bone screw, bone rod, bone dowel, pin, plate, dowel, hose, tube, thread, thread in a hose or tube, a bone anchor, a dental implant and a dental root implant.

19. The fixation device of claim 1, wherein no portion of the distal section overlaps the proximal section along a second direction perpendicular to the central axis.

* * * * *